United States Patent
Völker

(10) Patent No.: US 10,246,351 B2
(45) Date of Patent: Apr. 2, 2019

(54) DEVICE FOR PRODUCING ULTRAPURE WATER

(75) Inventor: Manfred Völker, Blankenbach (DE)

(73) Assignee: Vivonic GmbH, Sailauf (DE)

( * ) Notice: Subject to any disclaimer, the term of this patent is extended or adjusted under 35 U.S.C. 154(b) by 387 days.

(21) Appl. No.: 13/602,487

(22) Filed: Sep. 4, 2012

(65) Prior Publication Data
US 2013/0075310 A1  Mar. 28, 2013

(30) Foreign Application Priority Data

Sep. 24, 2011 (DE) .................. 10 2011 114 912

(51) Int. Cl.
*B01D 61/10* (2006.01)
*C02F 1/44* (2006.01)
(Continued)

(52) U.S. Cl.
CPC ............ *C02F 1/441* (2013.01); *A61M 1/168* (2013.01); *A61M 1/169* (2013.01); *A61M 1/1672* (2014.02); *B01D 61/025* (2013.01); *B01D 61/08* (2013.01); *B01D 61/12* (2013.01); *B01D 65/02* (2013.01); *B01D 65/10* (2013.01); *C02F 1/008* (2013.01); *A61M 1/1656* (2013.01); *A61M 1/1686* (2013.01); *A61M 2205/3306* (2013.01);
(Continued)

(58) Field of Classification Search
CPC ...... B01D 61/10; B01D 61/025; B01D 61/08; B01D 61/12; B01D 65/02; B01D 65/10; C02F 1/441; C02F 1/008; A61M 1/1672; A61M 1/168; A61M 1/169; A61M 1/1656; A61M 1/1686; A61M 2205/3306; A61M 2205/707; A61M 2205/7563

USPC ............................................... 210/85, 86, 94
See application file for complete search history.

(56) References Cited

U.S. PATENT DOCUMENTS 6,120,688 A * 9/2000 Daly .................. B01D 61/04
                                                    210/100
2002/0153319 A1* 10/2002 Mukhopadhyay ............ 210/652
(Continued)

FOREIGN PATENT DOCUMENTS

DE     3041209      5/1982
DE     3943631 C2   12/1990
(Continued)

OTHER PUBLICATIONS

English translated version of JP 06254552, description section.*
(Continued)

*Primary Examiner* — Heidi R Kelley
*Assistant Examiner* — Akash K Varma
(74) *Attorney, Agent, or Firm* — Greer, Burns & Crain, Ltd.

(57) ABSTRACT

The device for producing ultrapure water according to the reverse osmosis principle with a reverse osmosis filter which is subdivided by the RO membrane into a primary chamber and a secondary chamber, with a primary circuit through which raw water is supplied to the primary chamber and concentrate is discharged therefrom, and with a secondary circuit for supplying permeate to at least one consumer, preferably to a dialysis device, is characterized in that a means for detecting organic and/or inorganic deposits is arranged in or on the primary circuit and/or the secondary circuit and is connected to an evaluation means.

15 Claims, 4 Drawing Sheets

(51) Int. Cl.
*A61M 1/16* (2006.01)
*B01D 61/02* (2006.01)
*B01D 61/08* (2006.01)
*B01D 61/12* (2006.01)
*B01D 65/02* (2006.01)
*B01D 65/10* (2006.01)
*C02F 1/00* (2006.01)
*C02F 103/02* (2006.01)
*C02F 103/04* (2006.01)

(52) U.S. Cl.
CPC ............ *A61M 2205/707* (2013.01); *A61M 2205/7563* (2013.01); *B01D 2313/48* (2013.01); *B01D 2321/04* (2013.01); *B01D 2321/16* (2013.01); *B01D 2321/40* (2013.01); *C02F 2103/026* (2013.01); *C02F 2103/04* (2013.01); *C02F 2303/14* (2013.01); *C02F 2303/16* (2013.01); *C02F 2303/20* (2013.01); *C02F 2303/22* (2013.01)

(56) References Cited

U.S. PATENT DOCUMENTS

| | | | |
|---|---|---|---|
| 2004/0055955 | A1 | 3/2004 | Davis |
| 2006/0213821 | A1 | 9/2006 | Choi et al. |
| 2007/0086912 | A1* | 4/2007 | Dowling et al. ............. 422/1 |
| 2008/0164209 | A1* | 7/2008 | Zacerkowny et al. ........ 210/652 |
| 2010/0204924 | A1* | 8/2010 | Wolfe et al. ................ 702/25 |
| 2011/0049050 | A1* | 3/2011 | Scheu ............. B01D 61/025 210/637 |
| 2011/0100914 | A1* | 5/2011 | Mairal et al. ............. 210/651 |

FOREIGN PATENT DOCUMENTS

| | | | |
|---|---|---|---|
| DE | 4030913 | | 4/1992 |
| DE | 4222586 | | 7/1993 |
| DE | 19520916 | A1 | 1/1997 |
| DE | 19528160 | A1 | 1/1997 |
| DE | 20203733 | U1 | 6/2002 |
| DE | 10112719 | | 10/2002 |
| DE | 10256584 | | 5/2004 |
| DE | 10262036 | A1 | 6/2004 |
| DE | 10319196 | A1 | 7/2004 |
| DE | 10319221 | A1 | 7/2004 |
| DE | 102007018595 | B3 | 7/2008 |
| DE | 102008013109 | A1 | 9/2009 |
| DE | 102008036899 | | 2/2010 |
| DE | 102009031043 | A1 | 1/2011 |
| DE | 102009057562 | A1 | 6/2011 |
| DE | 102010048616 | A1 | 3/2012 |
| EP | 1431250 | A2 | 6/2004 |
| EP | 1440041 | | 7/2004 |
| EP | 1614437 | B1 | 1/2006 |
| JP | 06254552 | * | 9/1994 ............. B01D 36/00 |
| WO | 03106003 | | 12/2003 |

OTHER PUBLICATIONS

Search Report from Corresponding EP Application (11005886), dated Dec. 8, 2011.
Reference list from first Office Action in corresponding DE application, Mar. 15, 2012.
German Language Wikipedia: Umkehrosmose. Retrieved Jun. 26, 2012. Last Updated Jun. 20, 2012.
International Search Report from the European Patent Office, dated Jul. 22, 2011.

* cited by examiner

DEVICE FOR PRODUCING ULTRAPURE WATER

FIELD OF THE INVENTION

The present invention refers to a device for water treatment according to the reverse osmosis principle. Devices of such types, reverse osmosis or RO systems, are particularly used in combination with hemodialysis devices to recover ultrapure sterile water from tap water for preparing the dialysis fluid.

BACKGROUND

The operative principle of reverse osmosis systems consists in guiding the water to be prepared in a filter module under high pressure along the surface of a semipermeable membrane, with part of the water, the so-called permeate, passing through the membrane and being collected at the other side of the membrane and supplied to the consumption points. The part of the raw water that does not pass through the membrane and is enriched with retained substances, the so-called concentrate, flows at the end of the flow path of the primary chamber out of the membrane module.

As a typical example, the diagram shown in FIG. 1 illustrates the cooperation of essential functional elements of a reverse osmosis system according to the prior art. The raw water to be prepared flows out of the feed line 1 and via the valve 4 into a buffer vessel 5 with installed fill level control. The water passes out of the container 5 through the line 17 via the pump 6 into the reverse osmosis filter 7, the primary chamber 9 of which is separated by the semipermeable membrane 10 from the secondary chamber 8. The permeate flows out of the secondary chamber 8 into a ring line 15/16 from which the consumer lines 13 are branched off. At the end of the ring line, permeate produced in excess can flow via an inserted pressure holding valve 14 back into the vessel 5, the setting of said valve determining the pressure prevailing in the ring line 15/16.

The pressure that is needed for filtration and is prevailing in the primary chamber of the RO filter 9 is produced by the pump 6 in combination with a flow resistance means 11, e.g. in the form of a throttle valve or a pressure valve, which is inserted into the concentrate line 18 downstream of the filter.

The concentration difference of retained substances between outlet and inlet of the primary chamber 9 is of great importance to the function of the RO filter 7. At an excessively high concentration, particularly of calcium and magnesium, there is an increased risk that these constituents exceed a critical limit. The permeability of the membrane 10, and thus the permeate flow, will then decrease due to the formation of deposits, which means that the reverse osmosis filter will become useless prematurely.

Due to this fact especially the calcium and magnesium salts have so far been exchanged in consideration of the raw water quality by the upstream cation exchanger columns 2 for sodium. Ion exchangers are maintenance- and cost-intensive.

Sodium chloride and flushing water are needed for the reliable operation of the cation exchangers. Moreover, salt has to be refilled manually at regular intervals. In addition, the salt-containing flushing water contaminates the waste water.

Reverse osmoses serve particularly to obtain sterile water.

The part of the supplied tap water that does not pass through the membrane 10 and is enriched with retained chemical water constituents and bacteria will form a biofilm on the inner surfaces of the liquid-conducting system. The excretions of the biofilm may pass as pyrogens and endotoxins through the non-ideal membrane 10 and may contaminate the high-purity permeate circuit 15/16.

Therefore, it has so far been customary to carry out a thermal or chemical disinfection on reverse osmosis systems at regular intervals. To this end the operation is interrupted and thermal energy or chemical disinfectants are supplied to the system.

Due to the high risks that are particularly posed by chemical disinfection, the work steps have here to be monitored manually. This normally means considerable work.

SUMMARY

It is the object of the present invention to reduce the operating costs in that it is automatically determined when a chemical and/or thermal disinfection or cleaning of the primary circuit and/or secondary circuit and their lines and components, respectively, is needed.

This object is achieved according to the invention by the device for producing ultrapure water embodiments of which are described herein below.

DETAILED DESCRIPTION OF PREFERRED EMBODIMENTS

According to the invention a means for detecting 19 organic and/or inorganic deposits is arranged in or on the primary circuit and/or the secondary circuit, the detecting means 19 being connected to an evaluation means 20. The means detects deposits in the associated liquid line, preferably on the inner wall thereof, or on a component of the primary circuit or secondary circuit, e.g. inside the filter, and transmits the detected measurement values to an evaluation means which may be integrated into the control means of the RO system or of a connected dialysis device. The evaluation means 20 is expediently provided with a display means for the determined measurement values of the deposition layer, which is indicative of contamination. The device for producing ultrapure water contains a processor which controls all the production steps. The detection means 19 is connected to the processor. The evaluation means 20 is part of the processor.

Figure 1:
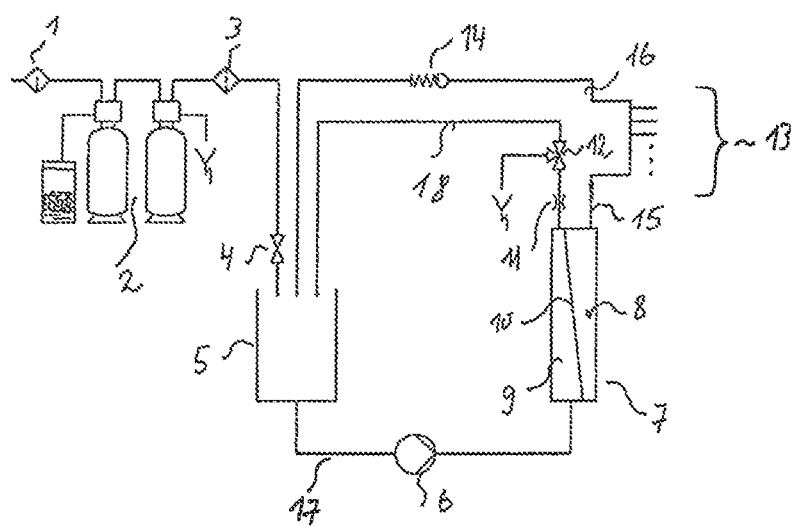
FIG. 1 is a schematic diagram of a prior art reverse osmosis device.
Figure 2:
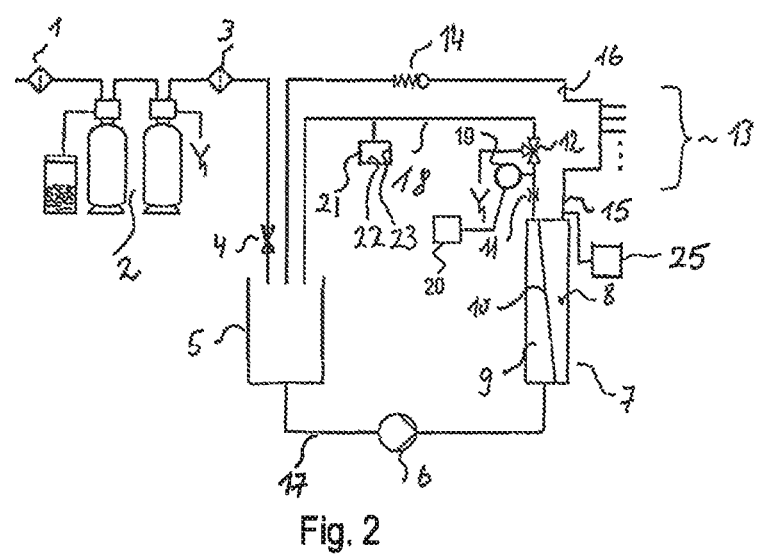
FIG. 2 is a schematic diagram of a first embodiment of a reverse osmosis device.
Figure 3:
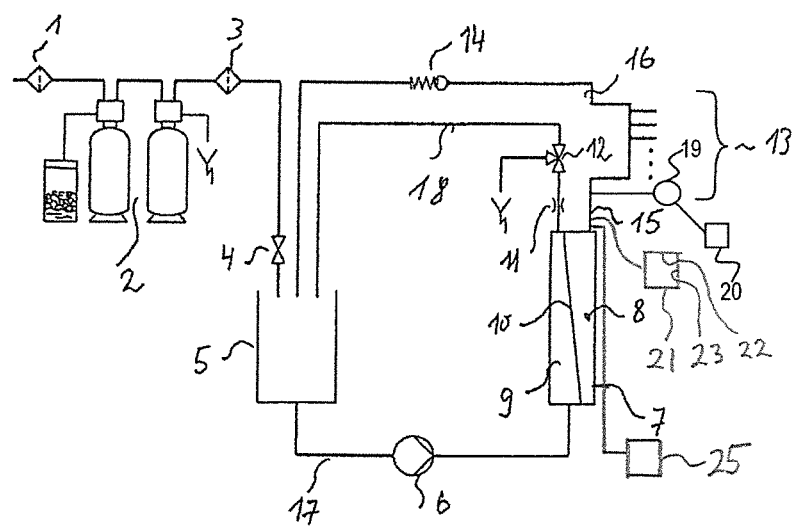
FIG. 3 is a schematic diagram of a second embodiment of a reverse osmosis device.
Figure 4:
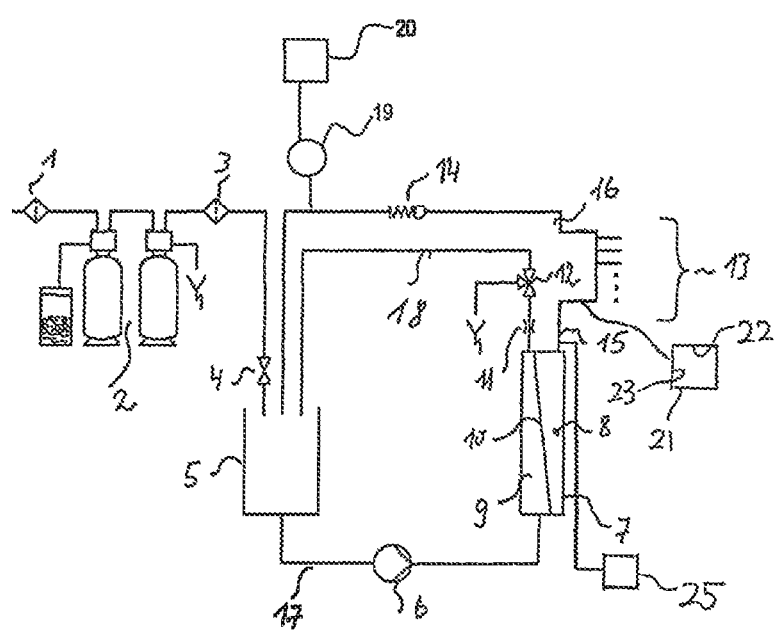
FIG. 4 is a schematic diagram of a third embodiment of a reverse osmosis device.

FIG. 2 illustrates one embodiment where the detecting means is in the primary circuit (1, 4, 5, 9, 17, 18). FIGS. 3 and 4, show other embodiments where the detecting means is in alternative locations in the secondary circuit (8, 15, 16). These embodiments are merely illustrative and other embodiments will be apparent to those skilled in the art and are within the scope of the invention.

Advantageously, it is provided that a limit value is predetermined for the determined measurement values and an alarm signal is produced when said limit value is reached (or exceeded), the alarm signal indicating that a chemical and/or thermal disinfection of the device has to be carried out.

As a result, these cleaning operations are not carried out at fixed times, as has so far been customary, but they are carried out when the determined deposits indicate that such a cleaning operation is now required. Overuse of cleaning processes can thereby be avoided on the one hand and it can be ensured on the other hand that the necessary cleaning process is carried out in case of an unforeseeable strong contamination, which may have multiple causes.

With great advantage it is provided that the means for detecting deposits comprises a sensor means which comprises a transmitter for transmitting optical signals and a receiver for the signals.

It may here also be provided that the optical signals transmitted by the transmitter are reflected by an opposite mirror means back to the optical receiver.

The quantity of the receiver signal is a direct function of the degree of soiling or the thickness of the deposition layer.

To determine the deposition of biological dirt layers, it may also be provided that said deposition reflects—by irradiation e.g. with UV light—a fluorescent measureable response signal corresponding to the layer thickness.

The liquid-conducting line which is provided with the sensor means can be designed with transparent or translucent material, whereby the transmitter, the receiver and optionally the mirror means may be arranged outside the line opposite to one another.

The contamination, particularly caused by limescale, can also be determined in another way than by a sensor means. In the case of systems of known volume which can be cleaned in a hot state, the soiling, particularly the limescale, can be determined on the heating surface in such a way that the energy input is evaluated as a measure of the soiling degree because in the case of a heating surface that is soiled or provided with a deposit the heat or energy input into the liquid takes more time.

With advantage the sensor system is installed in a measurement chamber 21 in which a surface 22 which is inert to contamination and which as a calibration and comparison surface determines the relative soiling degree is positioned next to a measurement surface 23.

With the invention it is possible to determine the times when a chemical or physical cleaning operation of the line system of the reverse osmosis device is needed by setting limit values to be determined in tests for deposits on permeate- or concentrate-conducting lines or components. This increases the reliability of the device and avoids unnecessary operating costs.

A particularly efficient form of the membrane cleaning process is here the reversal of the filtration direction on the semipermeable membrane 10 by means of a negative transmembrane pressure. For producing a negative transmembrane pressure a buffer vessel 25 of a flexible, expandable volume is installed in the permeate line 15.

In the case of a corresponding contamination the sensor system initiates backwashing in that the pump stops 6 and valve 12 opens to the outlet. Preferably, the flow resistance means 11 is opened or bridged by means of a bypass valve. The preloaded volume in the buffer vessel 25 flows here via the membrane 10 to the outlet and feeds the consumers 13 at the same time.

After a short backwashing operation the normal operation is resumed by activating the pump 6.

The invention claimed is:

1. A device for producing ultrapure water according to a reverse osmosis (RO) principle with a reverse osmosis filter which is subdivided by a RO membrane into a primary chamber and a secondary chamber, with a primary circuit through which raw water is supplied to the primary chamber and concentrate is discharged therefrom, and with a secondary circuit for supplying permeate to at least one consumer, the device for producing ultrapure water comprising,
   a pump connected to a conduit of the primary circuit upstream of the reverse osmosis filter;
   a flow resistance means and a valve with a discharge outlet connected to a concentrate conduit of the primary circuit downstream of the reverse osmosis filter;
   a deposition layer detector arranged in or on a concentrate line of the primary circuit downstream of the primary chamber that detects a deposition layer of at least one of organic and inorganic deposits, the deposition layer detector being connected to a processor, the processor including a deposition layer evaluator; and
   a buffer vessel having a flexible, expandable volume incorporated into a permeate conduit of the secondary circuit,
   wherein the deposition layer evaluator is configured to determine a thickness measurement value of the deposition layer detected by the deposition layer detector;
   wherein the deposition layer detector comprises a sensor system; and
   wherein the sensor system is configured to initiate a back flushing of the RO membrane when the determined thickness measurement value reaches a predetermined limit measurement value, wherein the back flushing comprises the deposition layer evaluator causing the processor to stop the pump and open the valve to the discharge outlet, and further causing the processor to control the buffer vessel to produce a negative pressure on the RO membrane to cause a reverse flow via the RO membrane to the discharge outlet.

2. The device according to claim 1, wherein the deposition layer evaluator is connected to a display for displaying the determined thickness measurement values.

3. The device according to claim 1, wherein the deposition layer evaluator outputs an alarm signal when the predetermined limit measurement value is reached or exceeded.

4. The device according to claim 1, wherein the sensor system comprises a transmitter for transmitting optical signals and a receiver for receiving incoming signals.

5. The device according to claim 4, wherein a mirror reflecting the optical signals is positioned opposite to the transmitter of the optical signals as a measurement surface that reflects the optical signals to the receiver.

6. The device according to claim 5, wherein a surface which is inert to deposits is positioned next to the measurement surface as a comparison or calibration surface.

7. The device according to claim 4, wherein the sensor system containing a section of a liquid-conducting line or of a component getting into contact with the liquid consists fully or partially of transparent or translucent material.

8. The device according to claim 4, wherein a sensor of the sensor system is installed in a measurement chamber.

9. The device according to claim 4, wherein the transmitter emits UV light for detecting deposition layers including biological deposits.

10. The device according to claim 1, wherein the deposit layer evaluator determines a thickness of the deposition layer, wherein the deposition layer comprises a biological and/or inorganic deposition.

11. A device for producing ultrapure water according to a reverse osmosis (RO) principle with a reverse osmosis filter which is subdivided by a RO membrane into a primary chamber and a secondary chamber, with a primary circuit through which raw water is supplied to the primary chamber and concentrate is discharged therefrom, and with a secondary circuit for supplying permeate to at least one consumer, the device for producing ultrapure water comprising, a pump connected to a conduit of the primary circuit upstream of the reverse osmosis filter;

a flow resistance means and a valve with a discharge outlet connected to a concentrate conduit of the primary circuit downstream of the reverse osmosis filter;

a deposition layer detector arranged in or on a ring line of the secondary circuit downstream of the secondary chamber that detects a deposition layer of at least one of organic and inorganic deposits, the deposition layer detector being connected to a processor, the processor including a deposition layer evaluator; and a buffer vessel having a flexible, expandable volume incorporated into a permeate conduit of the secondary circuit, wherein the deposition layer evaluator is configured to determine a thickness measurement value of the deposition layer detected by the deposition layer detector;

wherein the deposition layer detector comprises a sensor system; and wherein the sensor system is configured to initiate a back flushing of the RO membrane when the determined thickness measurement value reaches a predetermined limit measurement value, wherein the back flushing comprises the deposition layer evaluator causing the processor to stop the pump and open the valve to the discharge outlet, and further causing the processor to control the buffer vessel to produce a negative pressure on the RO membrane to cause a reverse flow via the RO membrane to the discharge outlet.

12. A device for producing ultrapure water according to a reverse osmosis (RO) principle with a reverse osmosis filter which is subdivided by a RO membrane into a primary chamber and a secondary chamber, with a primary circuit through which raw water is supplied to the primary chamber and concentrate is discharged therefrom, and with a secondary circuit for supplying permeate to at least one consumer, the device for producing ultrapure water comprising, a pump connected to a conduit of the primary circuit upstream of the reverse osmosis filter;

a flow resistance means and a valve with a discharge outlet connected to a concentrate conduit of the primary circuit downstream of the reverse osmosis filter;

a deposition layer detector arranged in or on a ring line of the secondary circuit downstream of a consumer line connected to the secondary chamber that detects a deposition layer of at least one of organic and inorganic deposits, the deposition layer detector being connected to a processor, the processor including a deposition deposit layer evaluator; and a buffer vessel having a flexible, expandable volume incorporated into a permeate conduit of the secondary circuit, wherein the deposition layer evaluator is configured to determine a thickness measurement value of the deposition layer detected by the deposition layer detector;

wherein the deposition layer detector comprises a sensor system; and wherein the sensor system is configured to initiate a back flushing of the RO membrane when the determined thickness measurement value reaches a predetermined limit measurement value, wherein the back flushing comprises the deposition layer evaluator causing the processor to stop the pump and open the valve to the discharge outlet, and further causing the processor to control the buffer vessel to produce a negative pressure on the RO membrane to cause a reverse flow via the RO membrane to the discharge outlet.

13. The device according to claim 1, wherein during said back flushing of the RO membrane, the buffer vessel continues to feed permeate to the consumer in addition to said causing reverse flow via the RO membrane to the discharge outlet.

14. The device according to claim 11, wherein during said back flushing of the RO membrane, the buffer vessel continues to feed permeate to the consumer in addition to said causing reverse flow via the RO membrane to the discharge outlet.

15. The device according to claim 12, wherein during said back flushing of the RO membrane, the buffer vessel continues to feed permeate to the consumer in addition to said causing reverse flow via the RO membrane to the discharge outlet.

* * * * *